(12) United States Patent  (10) Patent No.: US 6,997,043 B2
Swanson et al.  (45) Date of Patent: Feb. 14, 2006

(54) INTEGRATION OF ATMOSPHERIC INTRUSION SENSORS IN ELECTRONIC COMPONENT PACKAGES

(75) Inventors: Dale W. Swanson, Yorba Linda, CA (US); Len R. Enlow, Corona, CA (US); Anton B. Monge, Sunset Beach, CA (US)

(73) Assignee: The Boeing Company, Chicago, IL (US)

( * ) Notice: Subject to any disclaimer, the term of this patent is extended or adjusted under 35 U.S.C. 154(b) by 183 days.

(21) Appl. No.: 10/219,693

(22) Filed: Aug. 15, 2002

(65) Prior Publication Data

US 2004/0031339 A1  Feb. 19, 2004

(51) Int. Cl.
*G01M 3/16* (2006.01)
*H05K 5/06* (2006.01)

(52) U.S. Cl. ............... 73/49.3; 73/52; 361/683

(58) Field of Classification Search ........... 73/49.3, 73/40, 40.7, 52, 31.03, 865.9, 86; 361/752, 361/761, 683; 324/694–696; 422/53
See application file for complete search history.

(56) References Cited

U.S. PATENT DOCUMENTS 4,050,048 A  9/1977 Frazee 5,606,264 A  2/1997 Licari et al.

FOREIGN PATENT DOCUMENTS

| JP | 06307968 A | * 11/1994 |
| JP | 2000162081 A | * 6/2000 |
| JP | 2000171326 A | * 6/2000 |

OTHER PUBLICATIONS

Euopean Search Report mailed Jan. 10, 2005, 1 page.
Dale W. Swanson, Mary C. Chen, Boeing, and Leonard R. Enlow, Electronic Packaging Associates, "Evaluation of Moisture and Stress Sensor Chips in Single-Chip PEMs, Temperature Cycling, THB, HAST, and High-Temperature Storage/Operating Life Tests", Proceedings of the 1999 IMAPS Conference, Fall 1999. 7 pages, Dec. 1999.

* cited by examiner

*Primary Examiner*—Thomas P. Noland
(74) *Attorney, Agent, or Firm*—Harness Dickey & Pierce P.L.C.

(57) ABSTRACT

An apparatus for detecting an intrusion of an environmental substance into an environmentally sealed electronic components package. The electronic components package generally includes a plastic coated or plastic enclosed electronic component, that includes a printed circuit board and/or integrated circuits. The intrusion of the environmental substance into the electronic components package can be measured by one of a plurality of monitors. The monitors can detect the presence of the environmental substance and alert a user that a break in the seal of the electronic components package has occurred.

11 Claims, 2 Drawing Sheets

INTEGRATION OF ATMOSPHERIC INTRUSION SENSORS IN ELECTRONIC COMPONENT PACKAGES

FIELD OF THE INVENTION

The present invention relates to a system to ascertain the integrity of an electronic component, and particularly relates to a system to indicate moisture ingress for accumulation in a sealed system.

BACKGROUND OF THE INVENTION

Electronic components form a large part of many modern machines and devices. Furthermore, they are often integral to the proper operation of such devices. Electronic components often include, integrated circuits that provide a very compact and efficient means for performing various electronic functions.

Although integrated circuit boards and chips provide an inexpensive way to provide electronic components to many vehicles and structures, they are not always impervious to the elements such as moisture and other environmental contaminants that may harm electronic components. In particular, when these components are encased in plastic, different environmental conditions may damage the circuits. The plastic of the integrated circuits and chips are not completely impervious to moisture and environmental conditions. In addition, the plastic molded parts may be damaged or harmed by other environmental conditions such as thermal shock or extent of cracking. If the electronic components, such as integrated circuit boards, become damaged, then moisture may enter the enclosure surrounding circuit boards. If moisture is able to reach the circuit board interface, then damage may occur, particularly, by shorting or corroding the internal components.

One commonly known solution has been to use hermetically sealed components. Using hermetically sealed components, however, often greatly increases the cost of the component. These packages generally require specific and unique materials and manufacturing processes that have associated production costs. Although hermetically sealed components are generally known and accepted to have good seal longevity, it is desired to produce a component which is cheaper and still able to have a high longevity.

Moreover, it is easy to determine if a hermetically sealed component has been compromised. That is, determining that a hermetically sealed component has been damaged or the components inside the part where the seal may have been damaged could be determined by fine and gross leak testing. The same is not true for integrated circuits or similar components in plastic or other enclosures. Simply, there is no easy way to determine whether the electronic component package has been compromised, thus alerting a user to a possible or impending malfunction.

Therefore, it is desirable to produce a structure within the component package that is able to determine if a seal, designed to protect the electronic components from environmental conditions, has been compromised. Moreover, it is desired to form such a component from inexpensive and generally available integrated circuit chips that may be integrated into the circuit board, part, or enclosure (such as a box). Using generally availably components realizes cost reductions and inventory reduction which does not require specifically producing and formulating unique components for varying applications.

SUMMARY OF THE INVENTION

The present invention is directed to an apparatus for detecting moisture and associated environmental intrusions into an electronics package. Sensors determine whether moisture has entered an electronics package. In particular, sensors are used to determine the presence or absence of an electric current which in turn determines whether moisture is present. For example, a silver sensor is used to detect the gross or absolute intrusion of moisture into an electronics package. The presence of moisture causes silver ions to migrate and create an electrical short or conductive path in the sensor.

A first preferred embodiment of the present invention provides a system for monitoring a sealed electronics package for moisture or other elements that may have entered the sealed electronics package. The system includes an electronic component having a circuit. An envelope surrounds the electronic component and a monitor determines the integrity of the envelope. The monitor detects the presence of a substance in the envelope.

A second preferred embodiment of the present invention is directed to a system to provide substantial certainty in the detection of a substance that has entered an internal environment intended to be sealed from an external environment. The system includes a substantially sealed structure defining the internal environment. A component and a monitor are disposed in the internal environment. The monitor is able to determine the presence of a substance from the external environment in the internal environment.

A third embodiment of the present invention is directed to a system to determine whether an electronic components package is substantially free of an environmental substance. A structure defines an enclosed area substantially impermeable to the substance. An electronic component is disposed in the enclosed area. The electronic component becomes damaged when contacted by a critical concentration of the substance. A sensor is disposed in the enclosed area so that the monitor detects the presence of the substance before the substance reaches the critical concentration.

Further areas of applicability of the present invention will become apparent from the detailed description provided hereinafter. It should be understood that the detailed description and specific examples, while indicating the preferred embodiment(s) of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE EMBODIMENTS

The following description of the preferred embodiment(s) is merely exemplary in nature and is in no way intended to limit the invention, its application, or uses.

Figure 1:
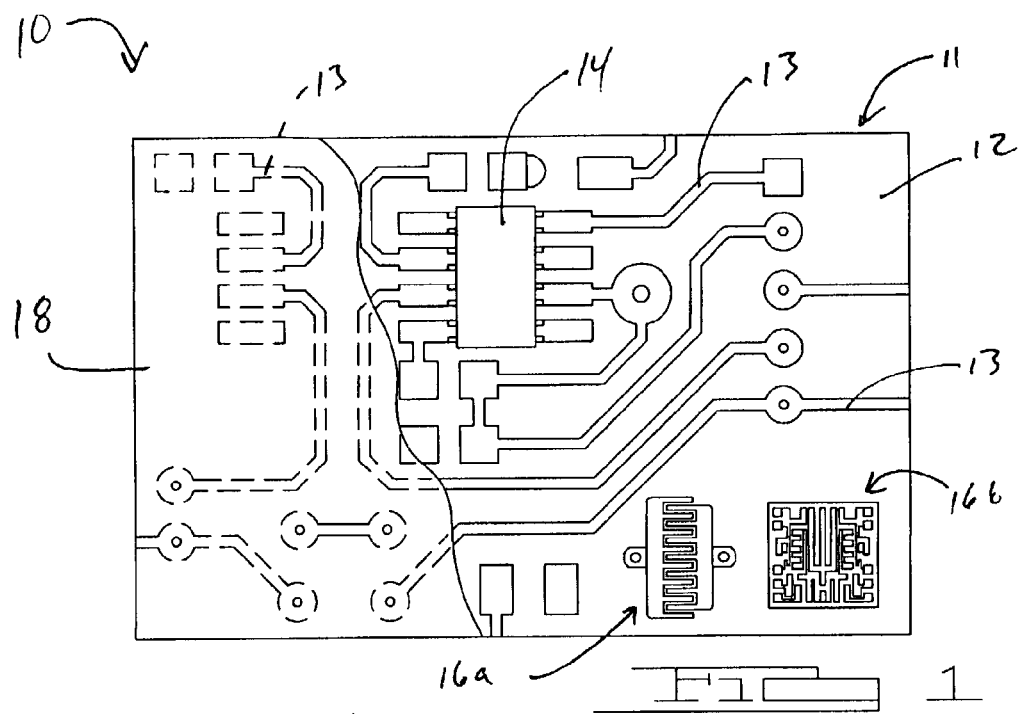
FIG. 1 is an elevated view of an exemplary electronic components package including a sensor, according to a first preferred embodiment of the present invention.

With reference to FIG. 1, a system 10 in accordance with a preferred embodiment of the present invention is shown for determining the integrity of an electronic components package 11. The electronics package 11, typically includes a printed circuit board (PCB) 12 having traces 13 or integrated circuits (ICs) 14, and is provided with a first seal failure monitor or sensor 16a and a second seal failure monitor or sensor 16b. Overlaying the PCB 12 is a sealing layer or portion 18 of an appropriate plastic such as an epoxy substance. The sealing portion 18 overlays or encases the entire PCB 12, or at least the portions that must be protected from environmental conditions or substances. The sealing portion 18, the PCB 12, and any associated ICs 14 are an example of the electronic component package 11.

It is desired to protect the PCB 12 and the accompanying components, such as the integrated circuits 14, and traces 13, from environmental conditions and substances. One environmental substance is moisture that may short or corrode the integrated circuits 14 or the traces 13 on the PCB 12. Therefore, a leak in the electronics component package 11 may be measured by the monitors 16a and 16b and corrected before damage occurs.

Although it may be inherently difficult to determine whether the electronic components package 11 includes a defect, either due to manufacture or wear, the appropriate monitors 16a and 16b may be included to determine if such a failure has occurred. Although many appropriate moisture sensors may be used, comb or interdigitated monitors are particularly well suited to providing simple and accurate detection of moisture in the electronic components package 11.

Figure 2:
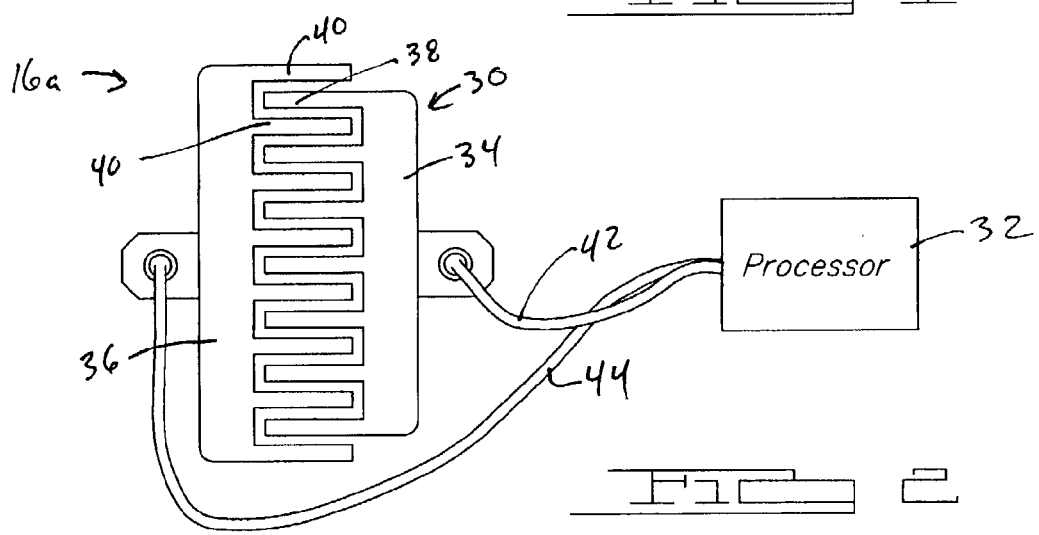
FIG. 2 is an enlarged and diagrammatic view of a substance monitor according to the first preferred embodiment of the present invention.

With reference to FIG. 2, the first monitor 16a is illustrated. The monitor 16a, illustrated in highly simplified form as a gross moisture sensor, includes a probe 30 and a processor 32. The probe 30 includes constituents such as silver. It will be understood that the probe 30 may be formed of many different constituents not including silver, but silver is particularly well suited for use in determining a gross moisture leak. The probe 30 generally includes an anode comb 34 and a cathode comb 36 that are in close proximity to each other. The anode comb 34 includes anode teeth or digits 38. Similarly, the cathode comb 34 includes cathode comb teeth or digits 40. The anode comb 34 and the cathode comb 36 are interdigitated, wherein each one of the anode digits 38 is disposed between two parallel, adjacent cathode digits 40. Also included are an anode lead 42 and a cathode lead 44 that interconnect the probe 30 and the processor 32. The processor 32 may then determine the presence or absence of a current in the probe 30. Also, external readings may be taken as to current that is transferred or being conducted between the anode comb 34 and the cathode comb 36.

The monitor 16a may be formed in an appropriate size for the application. Spacing between the associated digits 38, 40 may also be varied depending upon the requirements of the sensor 16a. The more space between associated digits the greater the time or amount of moisture to provide a signal. In one preferred implementation, the spacing between digits 38 and 40 is about 2 μm (0.08 mils) to about 25 μm (1 mil). It will also be understood that the sensor 16a illustrated in FIG. 2 is not illustrated to scale. The sensor 16a, when it is made of a silver compound on an IC, is generally square and preferably between about 40 and about 80 mils on a side.

Also, the sensor 16a may be integrated into the PCB 12. The combs 34 and 36 may be laid on the PCB 12 and the appropriate leads 42 and 44 affixed to the combs 34 and 36. Therefore, the sensor 16 may be provided on the PCB 12 without greatly increasing the size or weight of the PCB 12. This is particularly a concern in weight sensitive applications such as aircraft and space vehicles.

Alternatively, the monitor 16a may be first formed as a separate component IC and then added to the PCB 12. For example, the combs 34 and 36 may first be formed on a separate PCB and then added to the PCB 12 to provide a moisture sensor to the PCB 12. Nevertheless, the addition of this extra part does not tangibly increase the size or weight of the electronic components package 11. Moreover, the compact dimensions of the sensor 16a allows a plurality of sensors 16a to be added to an appropriate sized PCB 12 depending upon the size and distance between the moisture sensitive components.

The sensors 16a and 16b may be made more sensitive to moisture than other environmental conditions. Although it will be understood that other appropriate sensors may be used to detect other environmental leakages into the electronic components package 11. The sensor 16a, including a silver sensor, determines a gross amount or the absolute presence of any leak of moisture into the electronic components package 11. That is, any moisture leak, regardless of the degree, may be detected using the sensor 16a leading to a short. When the anode comb 34 and cathode comb 36 include silver ions, the silver ions become mobile when water is present between the digits 38 and 40 of the combs 34 and 36. Essentially, the silver sensor has substantially no current when there is no moisture present. Upon the presence of moisture on the silver sensor 16a, silver ions are able to transfer from one digit 38, 40 to another, thereby providing a current between the two combs 34, 36 of the silver sensor 16a. Therefore, the presence of generally any amount of moisture, which is able to interconnect two digits of the combs 34 and 36 the sensor 16a, causes a signal to be produced by the monitor 16a. The processor 32 provides a potential to the monitor 16a and detects a current flow from the anode comb 34 to the cathode comb 36, that only occurs when moisture is present. A user may then repair or replace the electronic components package 11 or any portion thereof.

Figure 3:
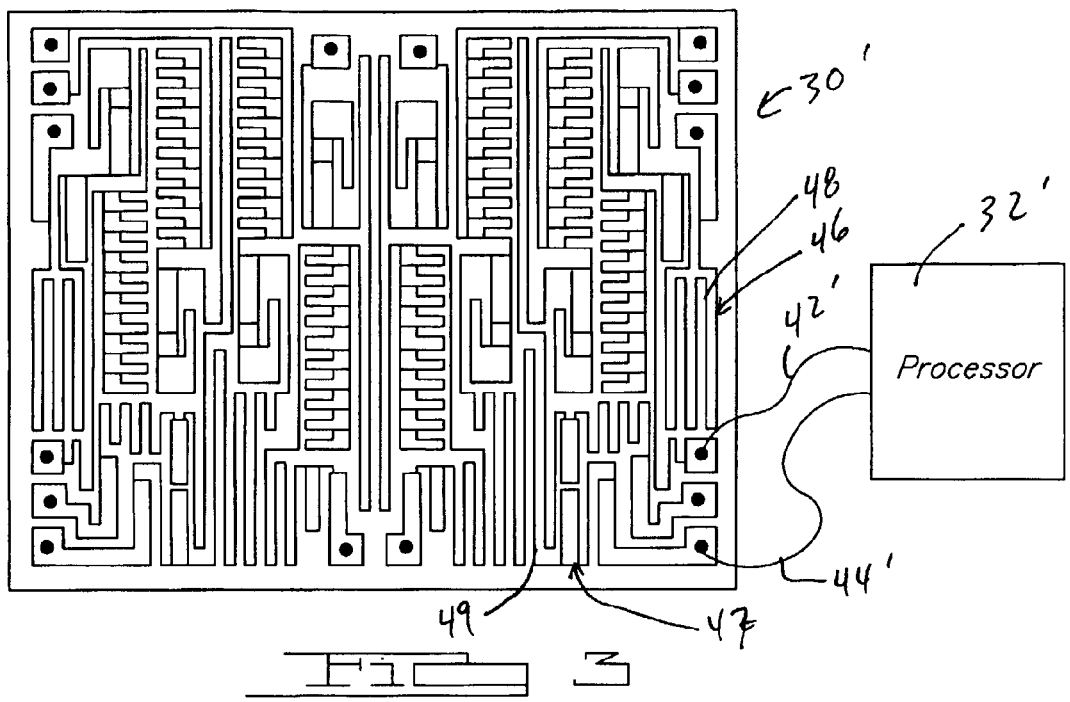
FIG. 3 is an enlarged and diagrammatic view of a substance monitor according to the first preferred embodiment of the present invention.

Second exemplary sensor 16b, illustrated in detail in FIG. 3, comprises a nichrome sensor. The nichrome sensor 16b includes a combination of nickel and chromium layers layered one atop the other. The nichrome sensor 16b is also relatively small and generally forms a rectangle having side lengths of preferably about 50 mills by about 100 mills. Again, it will be understood that the size of the nichrome sensor 16b may be altered depending upon the size necessary for the particular application.

The nichrome sensor 16b also includes an anode comb or labyrinth 46 and a cathode comb or labyrinth 47. The anode comb 46 includes anode digits 48 which are associated with cathode digits 49 of the cathode comb 47. The anode comb 46 may also include an anode lead 42' and the cathode comb a cathode lead 44' that interconnect the combs 46 and 47 to a processor 32'. Therefore, the combs 46 and 47 define a probe 30' that provides a signal, or which is used by the processor 30' to create a signal, based on the sensing of the probe 32'.

The nichrome sensor 16b comprises a more precise or quantitative moisture detector. In particular, the nichrome sensor 16b may determine quantitatively the amount of moisture which has leaked into the electronic components package 11. Therefore, at least two levels of moisture detection may be provided for the electronic components package 11. The silver sensor 16a provides a "gross" leak indication or absolute detection of whether moisture is present or not. The nichrome sensor 16b, on the other hand, can determine quantitatively the amount of moisture which has entered the electronic components package 11.

The nichrome sensor 16b provides a resistance output value when no moisture is present. The presence of moisture decreases the amount of resistance between the digits of the nichrome sensor 16b. Therefore, as the concentration of moisture increases, the resistance measured using the nichrome sensor 16b decreases. Therefore, a plot or determination of the amount of resistance in the nichrome sensor 16b depends upon the concentration of moisture, thus allowing a quantitative measurement of moisture.

In addition, other appropriate sensors may be used to determine moisture leaks. For example, an integrated microchip sensitive to corrosion can be used. One such chip is the ATC04 chip produced by Sandia®. The ATC04 is an integrated chip that includes ring oscillators as moisture and corrosion sensors and other sensors such as stress and temperature sensors. Nevertheless, the inclusion of such a chip in the electronic components package 11 can be used to determine whether the seal of the electronic components package 11 has become compromised.

Figure 4:
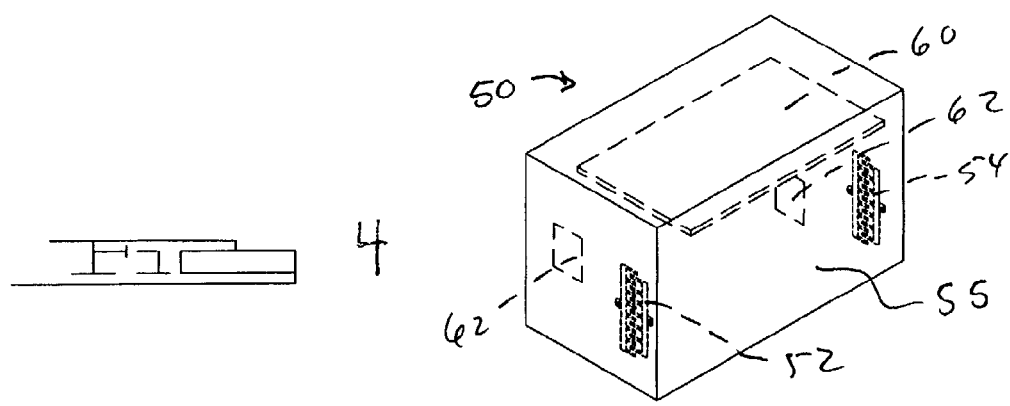
FIG. 4 is a perspective view of an electronics components package according to a second preferred embodiment of the present invention.

With reference to FIG. 4, an electronic components package 50 according to a second preferred embodiment of the present invention is illustrated. The electronic components package 50 includes a first moisture sensor 52 and a second moisture sensor 54 spaced a distance apart. The electronic package 50 includes a three dimensional box structure 55 that forms an enclosure or encasement of a sealed compartment that includes several PCBs 60 and other integrated circuit chips 62. The electronic components package 50, nevertheless, must be sealed from the outside ambient environment. Therefore, the presence of the moisture sensors 52 and 54 provide a means of measuring the amount of any moisture that enters the electronic components package 50.

Therefore, it will be understood that the moisture sensors 16a, 16b, 52 or 54 of the present invention may be used singly or as a plurality to determine the moisture present in an electronic components package or module. As an example, if the electronic components package is larger it may be desirable to include a plurality of moisture sensors in several different areas to determine whether moisture has entered any of those areas or might be affecting any of the circuitry in separate and selected areas. Conversely, if the electronic components package or module is substantially smaller, only one or two moisture sensors may be desired. In addition, different types of moisture sensors may be provided to measure both a gross moisture leakage and to quantify the amount of moisture which is present in the electronic component package.

Figure 5:
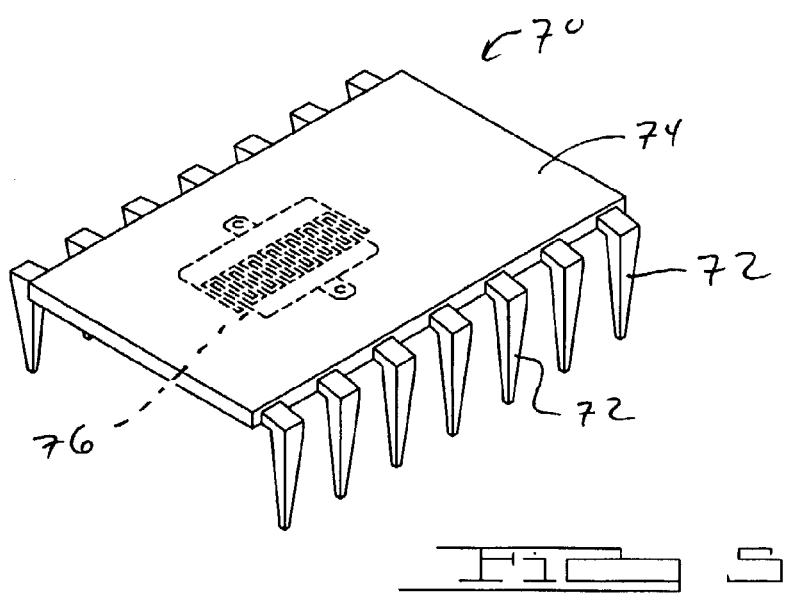
FIG. 5 is a perspective view of an electronics component package according to a third preferred embodiment of the present invention.

With reference to FIG. 5 an electronic components package 70 according to a third preferred embodiment of the present invention is illustrated. The electronic components package 70 generally includes an integrated circuit which may be soldered onto a PCB, such as the PCB 12. The electronic components package 70 includes a plurality of leads 72 which allow the interconnection between the PCB and the electronic components package 70. Any number of circuits or resistors may be included within the electronics component package 70. These components are then encapsulated or encased in a solid plastic case 74. Also encapsulated within the case 74 is a sensor 76. Although any number of the sensors 76 may be included, the electronic components package 70 is typically relatively small in size, and thus may only require one sensor 76. Nevertheless, it will be understood that the sensor 76 is highly functional and may be placed in a very small electronic components package 70.

With the present invention, electronic component packages or modules that have not been hermetically sealed may be used in sensitive applications. The use of moisture sensors allows an easy and quick means to determine whether the electronic component package seal has been compromised. From this determination, it is then known that moisture may be present that will likely disrupt the operation of the electronics in the electronic components package.

The description of the invention is merely exemplary in nature and, thus, variations that do not depart from the template of the invention are intended to be within the scope of the invention. Such variations are not to be regarded as a departure from the spirit and scope of the invention.

What is claimed is:

1. A sealed electronics system, the system comprising:
an electronic component including a circuit;
a casing surrounding said electronic component for forming an envelope that substantially seals the electronic component from an ambient environment;
a plurality of monitors disposed within said casing to determine whether an external substance has penetrated the envelope;
wherein a first monitor includes a silver constituent and a second monitor includes a corrosion sensitive system;
wherein said plurality of monitors includes at least three of a monitor including nichrome, a monitor including silver, and a monitor including a microprocessor.

2. A sealed electronics system, the system comprising:
an electronic component including a circuit;
a polymeric substance encasing said electronic component for forming an envelope that substantially seals the electronic component from an ambient environment;
a monitor disposed within said casing to determine whether an external substance has penetrated the envelope;
wherein said monitor includes a first gross monitor and a second quantitative monitor.

3. The system of claim 2, wherein said monitor includes:
a probe, wherein said probe includes a silver constituent; and
a processor to determine the presence of said external substance affecting said probe.

4. The system of claim 2, wherein said monitor comprises a monitor able to quantify an amount of the external substance that has penetrated said casing.

5. The system of claim 4, wherein said monitor includes:
a probe including at least one of the group consisting of: a nickel constituent and a chrome constituent;
a processor to determine the presence of the substance affecting said probe; and
wherein said processor produces a signal dependant upon the amount of the substance affecting said probe.

6. The system of claim 2, wherein said electronic component includes a printed circuit board and said printed circuit board includes traces formed in said printed circuit board; and wherein said casing includes a plastic overlaying said printed circuit board to substantially seal an area of said circuit board from an exterior ambient environment.

7. The system of claim 2, wherein the substance detected by said monitor includes water.

8. The system of claim 2, wherein said casing includes a structure defining an interior;

wherein said monitor includes a plurality of said monitors; and wherein one of said plurality of monitors is placed in said structure to determine the presence of a compromise in a selected portion of said casing.

9. The system of claim 2, wherein said monitor includes a first digitated member and a second digitated member;

wherein said first member and said second member are interdigitated.

10. The system of claim 9, wherein said digits of said first member are positioned a distance from said digits of said second member.

11. The system of claim 10, wherein said distance is about is about 2 $\mu$m to about 25 $\mu$m.

\* \* \* \* \*